(12) United States Patent
Gulstorff et al.

(10) Patent No.: US 10,820,122 B2
(45) Date of Patent: Oct. 27, 2020

(54) EMBEDDED ANTENNA

(71) Applicant: GN Hearing A/S, Ballerup (DK)

(72) Inventors: Steen Gulstorff, Ballerup (DK); Anders Heidemann Gregersen, Ballerup (DK)

(73) Assignee: GN Hearing A/S, Ballerup (DK)

( * ) Notice: Subject to any disclaimer, the term of this patent is extended or adjusted under 35 U.S.C. 154(b) by 0 days.

(21) Appl. No.: 15/364,277

(22) Filed: Nov. 30, 2016

(65) Prior Publication Data

US 2018/0146309 A1 May 24, 2018

(30) Foreign Application Priority Data

Nov. 18, 2016 (EP) .................................... 16199581

(51) Int. Cl.
  *H04R 25/00* (2006.01)
  *A61N 1/372* (2006.01)
  *A61N 1/36* (2006.01)

(52) U.S. Cl.
  CPC ....... *H04R 25/554* (2013.01); *A61N 1/37229* (2013.01); *A61N 1/36036* (2017.08); *H04R 25/60* (2013.01); *H04R 25/604* (2013.01); *H04R 2225/51* (2013.01); *H04R 2225/53* (2013.01); *H04R 2225/55* (2013.01)

(58) Field of Classification Search
  CPC .............. H04R 25/554; H04R 25/604; H04R 2225/551
  USPC ........... 381/315, 331; 607/57; 343/867, 788, 343/785; 235/492
  See application file for complete search history.

(56) References Cited

U.S. PATENT DOCUMENTS

| 9,680,209 B2 * | 6/2017 | Troelsen ................ H01Q 1/273 |
| 2005/0281425 A1 | 12/2005 | Greuet et al. |
| 2009/0046879 A1 * | 2/2009 | Knudsen ................ H01Q 1/243 381/315 |
| 2009/0143097 A1 | 6/2009 | Wilson |
| 2009/0323994 A1 * | 12/2009 | Makela ............. H04M 1/72591 381/331 |

(Continued)

FOREIGN PATENT DOCUMENTS

| EP | 2 466 916 A2 | 6/2012 |
| WO | WO 01/63964 A2 | 8/2001 |

OTHER PUBLICATIONS

European Search Report and Opinion, dated Apr. 21, 2017, for European Application No. EP 16199581 (Year: 2018).*

(Continued)

*Primary Examiner* — Phylesha Dabney
(74) *Attorney, Agent, or Firm* — Vista IP Law Group, LLP (57) ABSTRACT

A hearing prosthesis includes: a hearing loss processor configured to process an audio signal and compensate a hearing loss of a user of the hearing prosthesis, and output a hearing loss compensated audio signal based on the audio signal; an output transducer configured to convert the hearing loss compensated audio signal into an auditory output signal to be received by a human auditory system of the user; a near-field magnetic induction communication unit configured for wireless communication; and a magnetic field antenna operatively connected with the near-field magnetic induction communication unit; wherein at least a part of the magnetic field antenna is embedded in a multi-layer printed circuit board.

42 Claims, 5 Drawing Sheets

(56) References Cited

U.S. PATENT DOCUMENTS

2011/0101113 A1* 5/2011 Koujima ......... G06K 19/07771
235/492
2016/0375242 A1* 12/2016 Roehrlein .......... A61N 1/36032
607/57
2017/0028199 A1* 2/2017 Roehrlein ............ A61N 1/3787
2017/0245068 A1* 8/2017 Troelsen .............. H04R 25/554

OTHER PUBLICATIONS

Extended European Search Report dated May 2, 2017, for corresponding EP Patent Application No. 16199581.6, 10 pages.
Extended European Search Report dated Jun. 19, 2019, for corresponding EP Patent Application No. 19159402.7, 9 pages.

* cited by examiner

EMBEDDED ANTENNA

RELATED APPLICATION DATA

This application claims priority to, and the benefit of, European Patent Application No. 16199581.6 filed on Nov. 18, 2016, pending. The entire disclosure of the above application is expressly incorporated by reference herein.

FIELD OF TECHNOLOGY

A new hearing prosthesis is provided that is configured to perform wireless communication at reduced size and cost.

BACKGROUND

Near-Field Magnetic Induction (NFMI) communication utilizes a non-propagating magnetic field for communication between devices. A transmitter coil in one device modulates a magnetic field which is received and sensed by a receiver coil in another device.

NFMI communication systems differ from other types of wireless communication systems that use an antenna to generate and transmit an electromagnetic wave radiating outwardly into free space. The power density of the radiated electromagnetic wave decreases with distance to the antenna, namely proportional to the inverse of the distance to the second power ($1/r^2$) or −20 dB per decade, which facilitates long range communication.

NFMI communication systems have a short range (less than 2 meters).

The standard modulation schemes used in typical RF communications (amplitude modulation, phase modulation, and frequency modulation) can be used in NFMI communication systems.

NFMI communication systems are designed to contain transmission energy within the localized magnetic field. The magnetic field energy does not radiate into free space. The power density of nearfield transmissions decreases at a rate proportional to the inverse of the distance to the antenna to the sixth power ($1/r^6$) or −60 dB per decade.

In current commercial implementations of nearfield communications, the most commonly used carrier frequency is 13.56 MHz and has a wavelength λ of 22.1 meters.

The NFMI field is transmitted through human tissue with very little absorption as opposed to RF electromagnetic waves, making NFMI communication systems suitable for communication between devices residing at opposite ears of a human.

SUMMARY

A hearing prosthesis is provided comprising an electric circuit with
a hearing loss processor configured to process an audio signal and compensate a hearing loss of a user of the hearing prosthesis and output a hearing loss compensated audio signal based on the audio signal,
an output transducer configured to convert the hearing loss compensated audio signal into an auditory output signal that can be received by the human auditory system and resulting in the user hearing sound, and
a near-field magnetic induction communication unit configured for wireless communication, and
a magnetic field antenna operatively connected with the near-field magnetic induction communication unit,
characterized in that
at least a part of the magnetic field antenna is embedded in a multi-layer printed circuit board (PCB).

The hearing prosthesis may be a hearing aid of any type that is configured to be head worn at an ear of a user of the hearing aid, such as a Behind-The-Ear (BTE), a Receiver-In-the-Ear (RIE), an In-The-Ear (ITE), an In-The-Canal (ITC), a Completely-In-the-Canal (CIC), etc., hearing aid.

The hearing prosthesis may be an implantable device, such as a cochlear implant (CI) with an electrode array implanted in the cochlea for electronic stimulation of the cochlear nerve that carries auditory sensory information from the cochlea to the brain.

The hearing prosthesis is equipped with the near-field magnetic induction communication unit connected to the magnetic field antenna for local, i.e. short range, wireless communication that is not significantly attenuated by human tissue, e.g. between hearing prostheses worn on opposite sides of a head of a human, or between a unit of the hearing prosthesis worn on the outside of a head of a human and another unit of the hearing prosthesis implanted inside the head of the human.

Preferably, the magnetic field antenna comprises a coil and a magnetic core, preferably a ferrite core for provision of a strong magnetic field at low loss and low cost.

A printed circuit board (PCB) mechanically supports and electrically connects electronic components using conductive traces, pads and other features etched from conductive sheets or layers, typically copper sheets, laminated onto a non-conductive substrate. Components, such as capacitors, resistors, active devices, etc., are generally soldered on the PCB.

PCBs can be single sided with one conductive layer, double sided with two conductive layers or multi-layer with outer and inner conductive layers. Conductive traces on different layers are connected with vias, i.e. through-hole paths going through one or more adjacent layers for electrically interconnecting different conductive layers. The vias are typically made conductive by electroplating, or are lined with tubes or rivets. Multi-layer PCBs allow for much higher component density.

Multi-layer printed circuit boards have trace layers inside the board. This is achieved by laminating a stack of materials in a press by applying pressure and heat for a period of time. This results in an inseparable one piece multi-layer PCB. For example, a four-layer PCB can be fabricated by starting from a two-sided copper-clad laminate, etch the circuitry on both sides, then laminate to the top and bottom pre-preg and copper foil. It is then drilled, plated, and etched again to get traces on top and bottom layers.

Preferably, the ferrite core is embedded in the multi-layer printed circuit board whereby miniaturization is obtained at low cost.

Preferably, the coil includes conductive traces formed, e.g. by etching, in a conductive layer of the multi-layer printed circuit board for further ease of manufacture and reduction of cost.

Parts of conductive layers, e.g. forming ground planes, of the multi-layer printed circuit board may be used to provide magnetic shielding of electronic components such that the components are prevented from disturbing the magnetic field antenna. Shielding can be around other component or around the magnetic field antenna.

The near-field magnetic induction communication unit may also be embedded in the multi-layer printed circuit board facilitating further miniaturisation and cost reduction and ease of electrical interconnection of the near-field magnetic induction communication unit with the magnetic field antenna by conductive traces formed in conductive layers of the multi-layer printed circuit board.

The hearing loss processor may also be embedded in the multi-layer printed circuit board facilitating further miniaturisation and cost reduction and ease of electrical interconnection of the near-field magnetic induction communication unit with the hearing loss processor by conductive traces formed in conductive layers of the multi-layer printed circuit board.

The near-field magnetic induction communication unit may be configured for provision of the audio signal to the hearing loss processor.

The magnetic field antenna may be positioned in a housing of the hearing prosthesis so that, when the housing is worn at an ear of a user of the hearing prosthesis in its intended position during normal operation of the hearing prosthesis, a magnetic field generated by the magnetic field antenna is directed towards the other ear of the user of the hearing prosthesis.

The hearing prosthesis may be a cochlear implant with a transmitter housing to be attached to the head of a user and accommodating a NFMI transmitter for transmission of the hearing loss compensated audio signal to
a receiver accommodated in a receiver housing to be implanted underneath the skin for provision of the hearing loss compensated audio signal to an
electrode to be implanted in the cochlea of the user, based on the received hearing loss compensated audio signal, and wherein
the magnetic field antenna is positioned in at least one of the transmitter housing and the receiver housing of the cochlear implant so that, when the transmitter and receiver housings are worn in their intended positions for normal use at the head of the user, a magnetic field generated in the transmitter housing is directed towards the antenna of the receiver housing for optimum, or substantially optimum, reception.

The hearing prosthesis may comprise one or more microphones, each of which converts an acoustic signal applied to the microphone into a corresponding analogue audio signal in which the instantaneous voltage of the audio signal varies continuously with the sound pressure of the acoustic signal at the microphone.

The hearing prosthesis may also comprise a telecoil that converts a varying magnetic field at the telecoil into a corresponding varying analogue audio signal in which the instantaneous voltage of the audio signal varies continuously with the varying magnetic field strength at the telecoil.

Typically, the analogue audio signal is made suitable for digital signal processing by conversion into a corresponding digital audio signal in an analogue-to-digital converter whereby the amplitude of the analogue audio signal is represented by a binary number. In this way, a discrete-time and discrete-amplitude digital audio signal in the form of a sequence of digital values represents the continuous-time and continuous-amplitude analogue audio signal.

Throughout the present disclosure, the "audio signal" may be used to identify any analogue or digital signal forming part of the signal path from the output of the one or more microphones, telecoil, or near-field magnetic induction communication unit to an input of the hearing loss processor.

Throughout the present disclosure, the "hearing loss compensated audio signal" may be used to identify any analogue or digital signal forming part of the signal path from the output of the hearing loss processor to an input of the output transducer.

The output transducer may be a receiver, an implanted electrode of a cochlear implant, etc., configured to output an auditory output signal based on the hearing loss compensated audio signal, wherein the auditory output signal can be received by the human auditory system, whereby the user hears the sound.

The near-field magnetic induction communication unit may be a circuit comprising both a wireless transmitter and a wireless receiver. The transmitter and receiver may share common circuitry and/or a single die or housing.

Alternatively, the transmitter and receiver may share no circuitry, and the near-field magnetic induction communication unit may comprise separate dies or housings with the transmitter and the receiver, respectively.

The hearing prosthesis may advantageously be incorporated into a binaural hearing prosthesis system, wherein two hearing prostheses are interconnected, e.g., through a wireless network, for digital exchange of data, such as audio signals, signal processing parameters, control data, such as identification of signal processing programs, etc., etc., and optionally interconnected with other devices, such as a remote control, etc.

Signal processing in the new hearing prosthesis may be performed by dedicated hardware or may be performed in one or more signal processors, or performed in a combination of dedicated hardware and one or more signal processors.

As used herein, the terms "processor", "signal processor", "controller", "system", etc., are intended to refer to CPU-related entities, either hardware, a combination of hardware and software, software, or software in execution.

For example, a "processor", "signal processor", "controller", "system", etc., may be, but is not limited to being, a process running on a processor, a processor, an object, an executable file, a thread of execution, and/or a program.

By way of illustration, the terms "processor", "signal processor", "controller", "system", etc., designate both an application running on a processor and a hardware processor. One or more "processors", "signal processors", "controllers", "systems" and the like, or any combination hereof, may reside within a process and/or thread of execution, and one or more "processors", "signal processors", "controllers", "systems", etc., or any combination hereof, may be localized on one hardware processor, possibly in combination with other hardware circuitry, and/or distributed between two or more hardware processors, possibly in combination with other hardware circuitry.

Also, a processor (or similar terms) may be any component or any combination of components that is capable of performing signal processing. For examples, the signal processor may be an ASIC processor, a FPGA processor, a general purpose processor, a microprocessor, a circuit component, or an integrated circuit.

A hearing prosthesis includes: a hearing loss processor configured to process an audio signal and compensate a hearing loss of a user of the hearing prosthesis, and output a hearing loss compensated audio signal based on the audio signal; an output transducer configured to convert the hearing loss compensated audio signal into an auditory output signal to be received by a human auditory system of the user; a near-field magnetic induction communication unit configured for wireless communication; and a magnetic field antenna operatively connected with the near-field magnetic induction communication unit; wherein at least a part of the magnetic field antenna is embedded in a multi-layer printed circuit board.

Optionally, the near-field magnetic induction communication unit is embedded in the multi-layer printed circuit board, and wherein the multi-layer printed circuit board holds conductive traces for electrical interconnection of the near-field magnetic induction communication unit with the magnetic field antenna.

Optionally, the multi-layer printed circuit board comprises a conductive layer configured for magnetic shielding of the magnetic field antenna.

Optionally, the hearing loss processor is embedded in the multi-layer printed circuit board.

Optionally, the magnetic field antenna comprises a coil and a ferrite core.

Optionally, the ferrite core is embedded in the multi-layer printed circuit board.

Optionally, the coil includes conductive traces formed in a conductive layer of the multi-layer printed circuit board.

Optionally, the near-field magnetic induction communication unit is configured for provision of the audio signal.

Optionally, the hearing prosthesis further includes a microphone configured for conversion of an acoustic signal received at the microphone into the audio signal and, for provision of the audio signal.

Optionally, the hearing prosthesis further includes a housing, wherein the magnetic field antenna is positioned in the housing of the hearing prosthesis such that, when the housing is worn at an ear of the user of the hearing prosthesis in its intended position during operation of the hearing prosthesis, a magnetic field generated by the magnetic field antenna will be directed towards the other ear of the user of the hearing prosthesis.

Optionally, the hearing prosthesis is a cochlear implant comprising: a transmitter housing to be attached to a head of the user, the transmitter housing configured for accommodating a transmitter for transmission of the hearing loss compensated audio signal; and a receiver accommodated in a receiver housing to be implanted underneath a skin for receiving the hearing loss compensated audio signal, and for providing the hearing loss compensated audio signal to an electrode to be implanted in a cochlea of the user; wherein the magnetic field antenna is positioned in at least one of the transmitter housing and the receiver housing of the cochlear implant so that, when the transmitter housing and the receiver housing are worn in their intended positions at the head of the user, a magnetic field generated in the transmitter housing is directed towards the antenna that is accommodated by the receiver housing.

Other features, advantageous, and/or embodiments will be described in the detailed description.

BRIEF DESCRIPTION OF THE DRAWINGS

In the following, the new hearing prosthesis is explained in more detail with reference to the drawings, wherein FIG. 1 is a schematic diagram of an exemplary hearing prosthesis circuitry, FIG. 2 schematically illustrates an embedded magnetic field antenna, and FIG. 3 schematically illustrates an embedded magnetic field antenna and an embedded near-field magnetic induction communication unit, FIG. 4 schematically illustrates the position of an embedded magnetic field antenna in a BTE hearing aid when mounted in its intended operational position behind an ear of a user, and FIG. 5 schematically illustrates the position of an embedded magnetic field antenna in a transmitter of a cochlear implant.

DETAILED DESCRIPTION

Various features are described hereinafter with reference to the figures. It should be noted that the elements of similar structures or functions are represented by like reference numerals throughout the figures. Like elements will, thus, not be described in detail with respect to the description of each figure. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated, or if not so explicitly described.

In the following, various examples of the new hearing prosthesis are illustrated. The new hearing prosthesis according to the appended claims may, however, be embodied in different forms and should not be construed as limited to the examples set forth herein.

Figure 1:
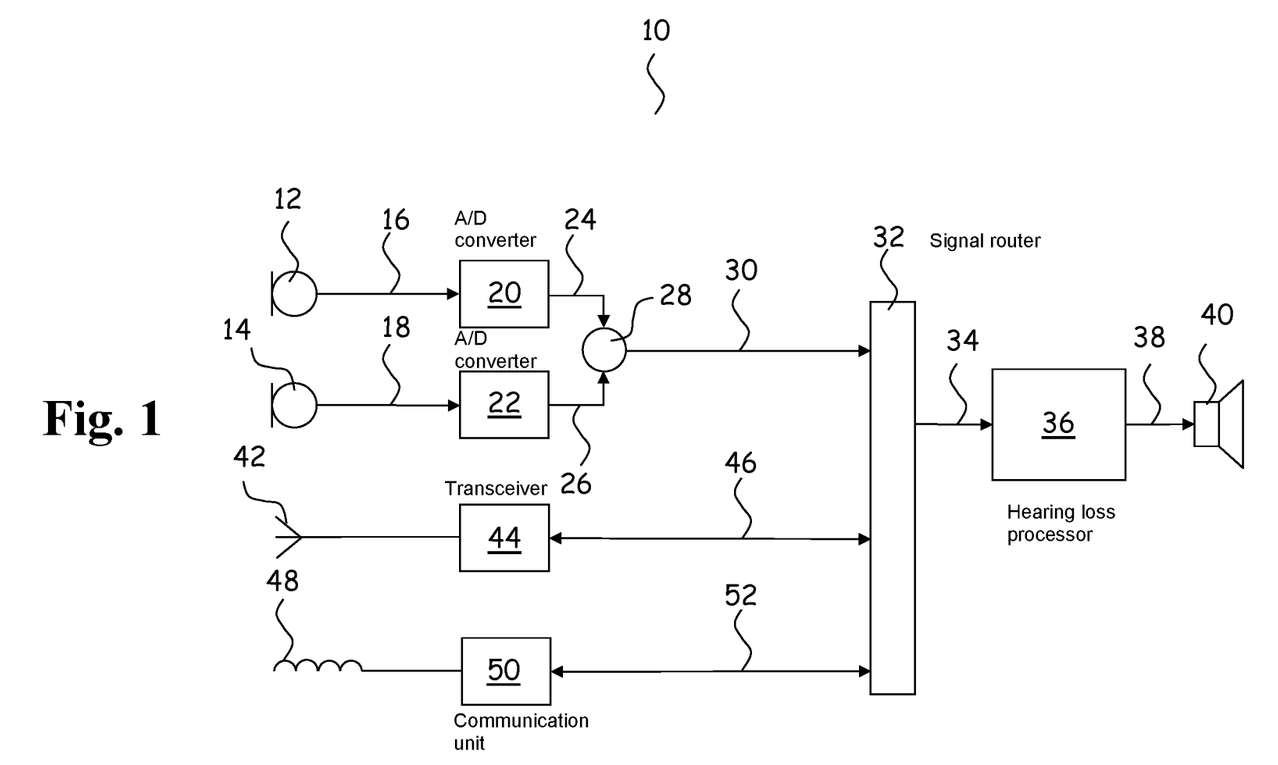

FIG. 1 schematically illustrates exemplary hearing prosthesis circuitry 10 of the new hearing prosthesis. The illustrated new hearing prosthesis is a hearing aid that may be of any suitable mechanical design, e.g. to be worn in the ear canal, or partly in the ear canal, behind the ear or in the concha, such as the well-known types: BTE, ITE, ITC, CIC, etc.

The illustrated hearing prosthesis circuitry 10 comprises a front microphone 12 and a rear microphone 14 for conversion of an acoustic sound signal from the surroundings into corresponding microphone audio signals 16, 18 output by the microphones 12, 14. The microphone audio signals 16, 18 are digitized in respective A/D converters 20, 22 for conversion of the respective microphone audio signals 16, 18 into respective digital microphone audio signals 24, 26 that are optionally pre-filtered (pre-filters not shown) and combined in signal combiner 28, for example for formation of a digital microphone audio signal 30 with directionality as is well-known in the art of hearing prostheses. The digital microphone audio signal 30 is input to the signal router 32 configured to output a weighted sum 34 of signals input to the signal router 32. The signal router output 34 is input to a hearing loss processor 36 configured to generate a hearing loss compensated output signal 38 based on the signal router output 34. The hearing loss compensated output signal 38 is input to a receiver 40 for conversion into acoustic sound for transmission towards an eardrum (not shown) of a user of the hearing aid.

The illustrated hearing prosthesis circuitry 10 is further configured to receive data, including control signals and digital audio from various transmitters, such as mobile phones, smartphones, desktop computers, tablets, laptops, radios, media players, companion microphones, broadcasting systems, such as in a public place, e.g. in a church, an auditorium, a theatre, a cinema, etc., public address systems, such as in a railway station, an airport, a shopping mall, etc., etc.

In the illustrated example, data including digital audio is transmitted wirelessly to the hearing prosthesis and received by the hearing prosthesis RF-antenna 42 connected to a RF-transceiver 44. The RF-transceiver 44 retrieves the digital data 46 from the received RF-transceiver signal, including the digital audio representing a stereo audio signal or a mono audio signal. The signal router 32 is also configured to route the stereo channel (or the mono audio signal) intended for a hearing prosthesis at the other ear of the user to the near-field magnetic induction communication unit 50 that modulates the digital audio 52 of the stereo channel in question (or the mono audio signal) into a modulated signal suitable for transmission via the embedded ferrite antenna 48 that emits a local, non-propagating magnetic field in the direction of the other hearing prosthesis (not shown) with field lines aligned with a ferrite core of a ferrite antenna in a housing of the other hearing prosthesis for optimum, or substantially optimum, reception when both hearing prostheses are worn in their intended operational positions at the respective ears of the user during normal operation.

The other hearing prosthesis may have the same circuitry 10 as shown in FIG. 1, wherein the ferrite antenna 48 receives the modulated magnetic field and converts it into a voltage that is output to the near-field magnetic induction communication unit 50 that is configured to demodulate the digital audio 52 of the stereo channel (or the mono audio signal) and forward it to the signal router 32 to include the digital audio 52 of the stereo channel (or the mono audio signal) in the audio signal 34 that is input to the hearing loss processor 36 for hearing loss compensation.

In this way, the digital audio 52 of the stereo channel (or the mono audio signal) for the other ear is transmitted to the hearing prosthesis at the other ear with little attenuation.

The digital audio 46 may include audio from a plurality of sources and thus, the digital audio 46 may form a plurality of input signals for the signal router 32, one input signal for each source of audio.

In the event of receipt of digital audio by the RF-antenna 42, the digital audio 46 may be transmitted to the user while the other signal 30 is attenuated during transmission of the digital audio. The other signal 30 may also be muted. The user may enter a command through a user interface of the hearing prosthesis of a type well-known in the art, controlling whether the other signal 30 is muted, attenuated, or remains unchanged.

Figure 2:
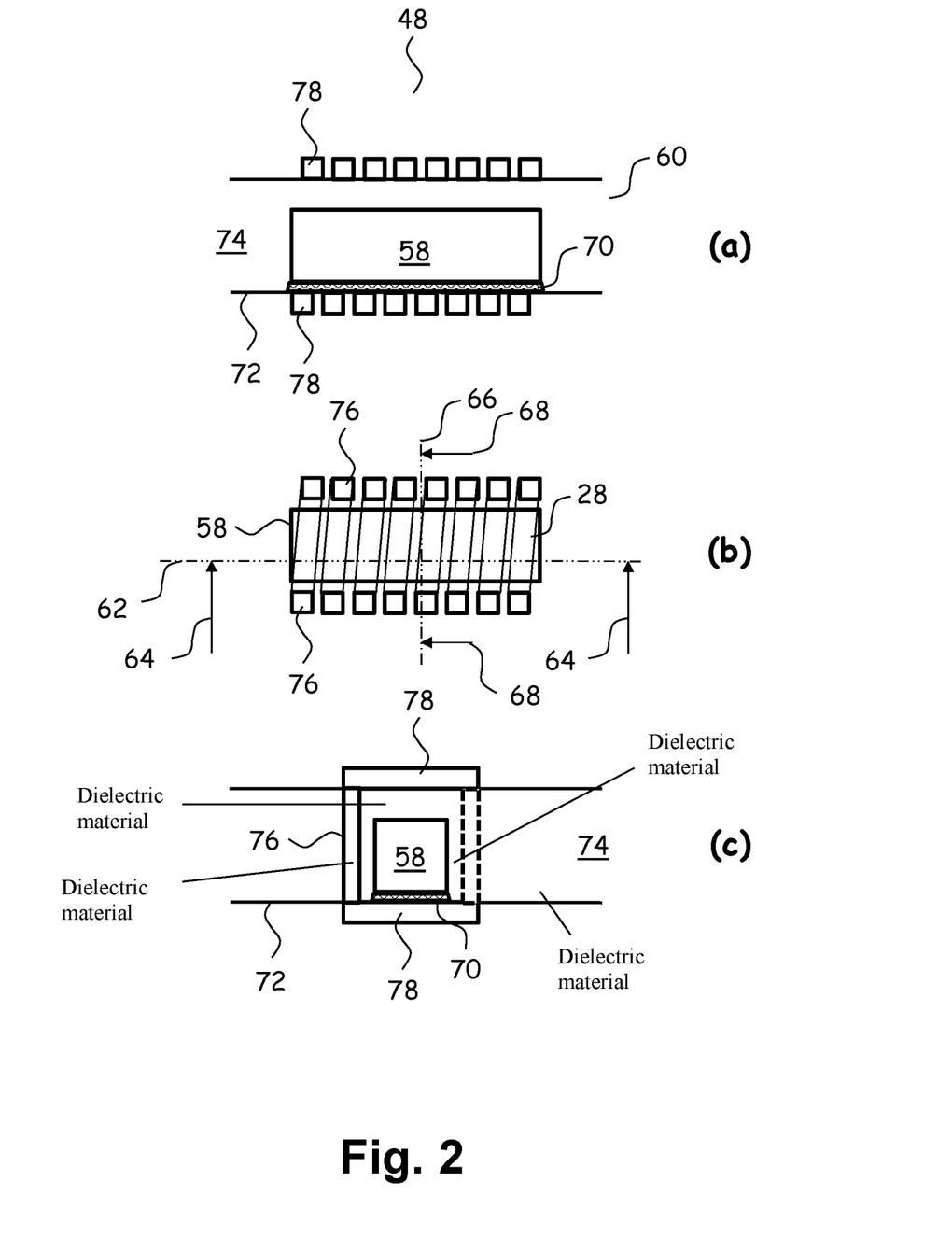

FIG. 2 schematically illustrates an embedded magnetic field antenna 48 with an embedded ferrite core 58 The embedded magnetic field antenna 48 is included in a hearing prosthesis (not shown) for provision of local, i.e. short range, wireless communication that is not significantly attenuated by human tissue, e.g. between hearing prostheses worn on opposite sides of a head of a human, or between a unit of the hearing prosthesis worn on the outside of a head of a human and another unit of the hearing prosthesis implanted inside the head of the human. The illustrated magnetic field antenna 48 comprises a coil and a ferrite core 58 for provision of a strong magnetic field at low loss and low cost. The embedding of the ferrite core 58 in the multi-layer printed circuit board 60 leads to miniaturization at low cost.

The coil includes conductors formed by metallized through holes 76 and interconnected with conductive traces 78 formed in, e.g. by etching, conductive layers of the multi-layer printed circuit board for further ease of manufacture and reduction of cost.

FIG. 2(a) shows the antenna 48 from the side in a cross-section perpendicular to a plane of the multi-layer printed circuit board 60, and along the length of the ferrite core 58.

FIG. 2(b) shows a top view of the antenna 48, wherein the line 62 indicates the position of the cross-section shown in FIG. 2(a) and the arrows 64 show the viewing direction of FIG. 2(a).

FIG. 2(c) shows the antenna 48 in a cross-section perpendicular to the length of the ferrite core 58 along the line 66 shown in FIG. 2(b) in the viewing direction indicated by arrows 68.

The ferrite core 58 is embedded in the multi-layer printed circuit board 60 in a way similar to the well-known embedding technology utilized for chip embedding with use of standard printed circuit board manufacturing processes.

In one example, the ferrite core 58 is initially applied and glued 70 to a core substrate 72. Then a dielectric fill material 74, e.g. a resin coated copper (RCC), is vacuum laminated on the core substrate 72 for void free distribution of the dielectric material 74. Preferably, the resin formulation is adjusted so that its thermo-mechanical properties correspond to the thermo-mechanical properties of the ferrite core 58. Then through holes 76 are made, e.g. by laser drilling, followed by copper metallization for formation of electrical connections between the two sides of the PCB having the ferrite core 58 between them. The metallized through holes 76 form part of the coil that winds around the ferrite core 58. Finally, conductive trace lines 78 are formed of the copper coating of the two sides of the PCB opposite the ferrite core 58 for formation of the remaining parts of the coil that winds around the ferrite core and forms the antenna 48 together with the ferrite core 58.

Figure 3A:
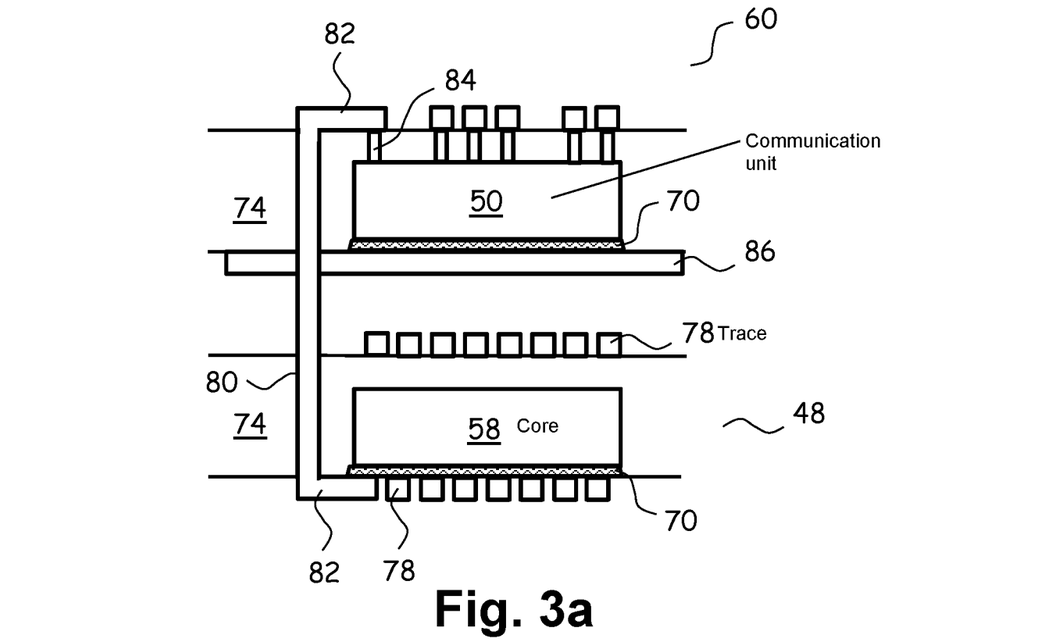
Figure 3B:
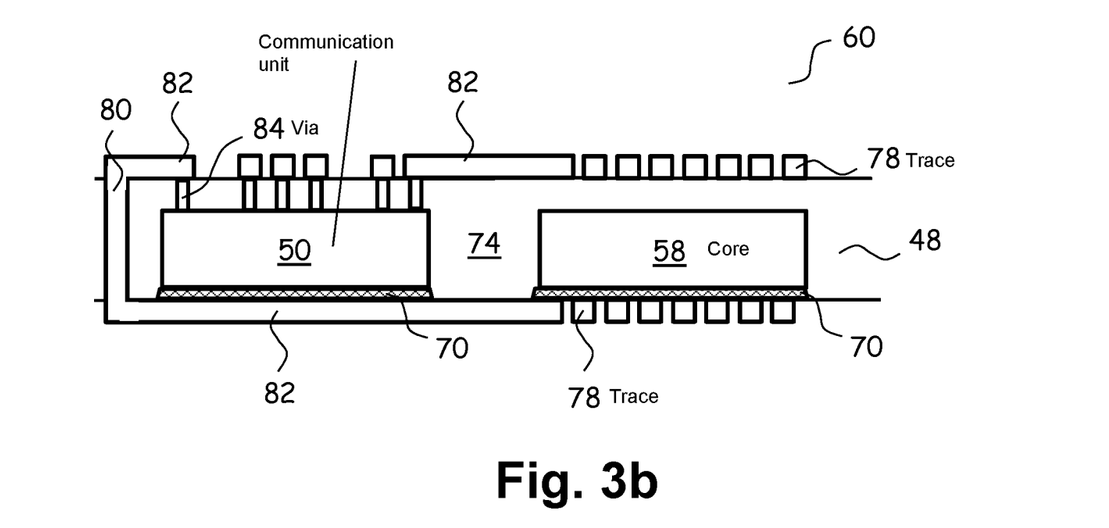

FIG. 3 schematically illustrates an embedded magnetic field antenna 48 operatively connected with an embedded near-field magnetic induction communication unit 50. A stacked configuration is illustrated in FIG. 3 (a) whereas the ferrite core 58 of the magnetic field antenna 48 and the near-field magnetic induction communication unit 50 are embedded in the same layer of the printed circuit board in FIG. 3 (b).

In FIGS. 3 (a) and 3 (b), the near-field magnetic induction communication unit 50 is also embedded in the multi-layer printed circuit board 60 facilitating further miniaturisation and cost reduction and ease of electrical interconnection of the near-field magnetic induction communication unit 50 with the magnetic field antenna 48 by through holes 80, metallized micro-vias 84 connected to chip bond pads of the unit 50, and conductive traces 82 formed in conductive layers of the multi-layer printed circuit board 60.

The embedding of the near-field magnetic induction communication unit 50 and near-field magnetic induction communication unit 50 in the multi-layer printed circuit board 60 is realized with multiple bonding and lamination steps of the type disclosed above in connection with FIG. 2.

In FIG. 3 (a), a conductive layer 86 forming a ground plane is provided in the multi-layer printed circuit board 60 to obtain magnetic shielding of electronic circuitry located above the magnetic shield 86 and opposite the magnetic field antenna 48 such that the circuitry is prevented from affecting the magnetic field antenna 48.

Figure 4:
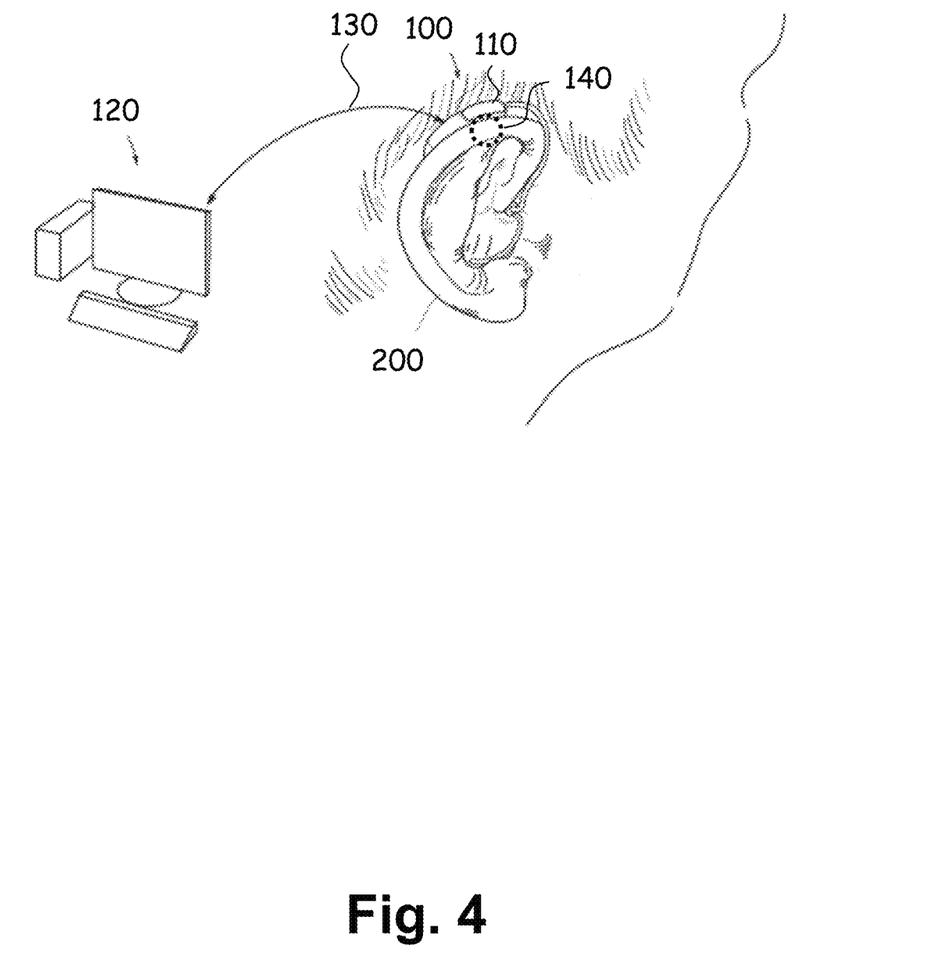

FIG. 4 shows a hearing prosthesis 100 in the form of a Behind-The-Ear hearing aid 100 mounted in its intended operating position for normal use, i.e. with its BTE housing 110 mounted behind the ear, i.e. behind the pinna 200, of the user. The BTE housing 110 of the illustrated Behind-The-Ear hearing aid 100 accommodates the hearing prosthesis circuitry 10 shown in FIG. 1.

The illustrated Behind-The-Ear hearing aid 100 forms part of a binaural hearing prosthesis system with a similar second Behind-The-Ear hearing aid (not visible) mounted at the other ear (not visible) of the user.

The second Behind-The-Ear hearing aid (not visible) also comprises the hearing prosthesis circuitry 10 shown in FIG. 1.

FIG. 4 also schematically illustrates a desktop computer 120 that is configured for wireless transmission 130 of data relating to a hardware and/or software configuration of the Behind-The-Ear hearing aid 100, e.g. utilizing the Bluetooth LE protocol, to the Behind-The-Ear hearing aid 100 for adjustment of various parameters of the Behind-The-Ear hearing aid 100.

Further, the desktop computer 120 is configured for wireless streaming of multi-channel audio, e.g. two-channel stereo, multi-channel surround sound, multi-channel teleconference audio, virtual reality 3D sound, etc., to the Behind-The-Ear hearing aid 100.

The Behind-The-Ear hearing aid 100 is also configured to receive data, including control signals and digital audio from various other transmitters (not shown), such as mobile phones, smartphones, desktop computers, tablets, laptops, radios, media players, companion microphones, broadcasting systems, such as in a public place, e.g. in a church, an auditorium, a theatre, a cinema, etc., public address systems, such as in a railway station, an airport, a shopping mall, etc., etc.

In FIG. 4, data, including digital audio, that are transmitted wirelessly 130 to the Behind-The-Ear hearing aid 100 are received by the Behind-The-Ear hearing aid RF-antenna 42, see FIG. 1, connected to a RF-transceiver 44, see FIG. 1. The RF-transceiver 44, see FIG. 1, retrieves the digital data 46, see FIG. 1, from the received RF-transceiver signal, including the digital audio, e.g., representing a stereo audio signal, or a mono audio signal. The signal router 32, see FIG. 1, is also configured to route the stereo channel or mono audio signal intended for the second Behind-The-Ear hearing aid mounted at the other ear of the user to the near-field magnetic induction communication unit 50, see FIG. 1, that modulates the digital audio 52, see FIG. 1, of the stereo channel in question (or the mono audio signal) into a modulated signal suitable for transmission via the embedded ferrite antenna 48, see FIG. 1, that emits a local, non-propagating magnetic field in the direction of the second Behind-The-Ear hearing aid (not visible) with field lines aligned with a ferrite core of a ferrite antenna in a housing of the second Behind-The-Ear hearing aid for optimum, or substantially optimum, reception when both hearing aids are worn in their intended operational positions at the respective ears of the user during normal operation.

The dotted circle 140 indicates the orientation of the coil having windings around the ferrite core (not visible) of the embedded ferrite antenna (not visible). The orientation of the coil is substantially perpendicular to the longitudinal extension or direction of the ferrite core which is aligned with the ferrite core of the ferrite antenna in the housing of the second Behind-The-Hearing aid (not visible) for optimum, or substantially optimum, reception.

In the second Behind-The-Hearing aid (not visible) with the circuitry 10 shown in FIG. 1, the ferrite antenna of the second Behind-The-Hearing aid receives the modulated magnetic field and converts it into a voltage that is output to the near-field magnetic induction communication unit that is configured to demodulate the digital audio of the stereo channel (or the mono audio signal) and forward it to the signal router to include the digital audio of the stereo channel (or the mono audio signal) in the audio signal that is input to the hearing loss processor for hearing loss compensation.

In this way, the digital audio of the stereo channel (or the mono audio signal) for the other ear is transmitted to the second Behind-The-Ear hearing aid at the other ear with little attenuation.

As already mentioned, the digital audio may include audio from a plurality of sources and thus, the digital audio may form a plurality of input signals for the signal router, one input signal for each source of audio.

In the event of receipt of digital audio by the RF-antenna, the digital audio may be transmitted to the user while other audio signals are attenuated during transmission of the digital audio. The other signals may also be muted. The user may enter a command through a user interface of the Behind-The-Ear hearing aid of a type well-known in the art, controlling whether the other signal is muted, attenuated, or remains unchanged.

Figure 5:
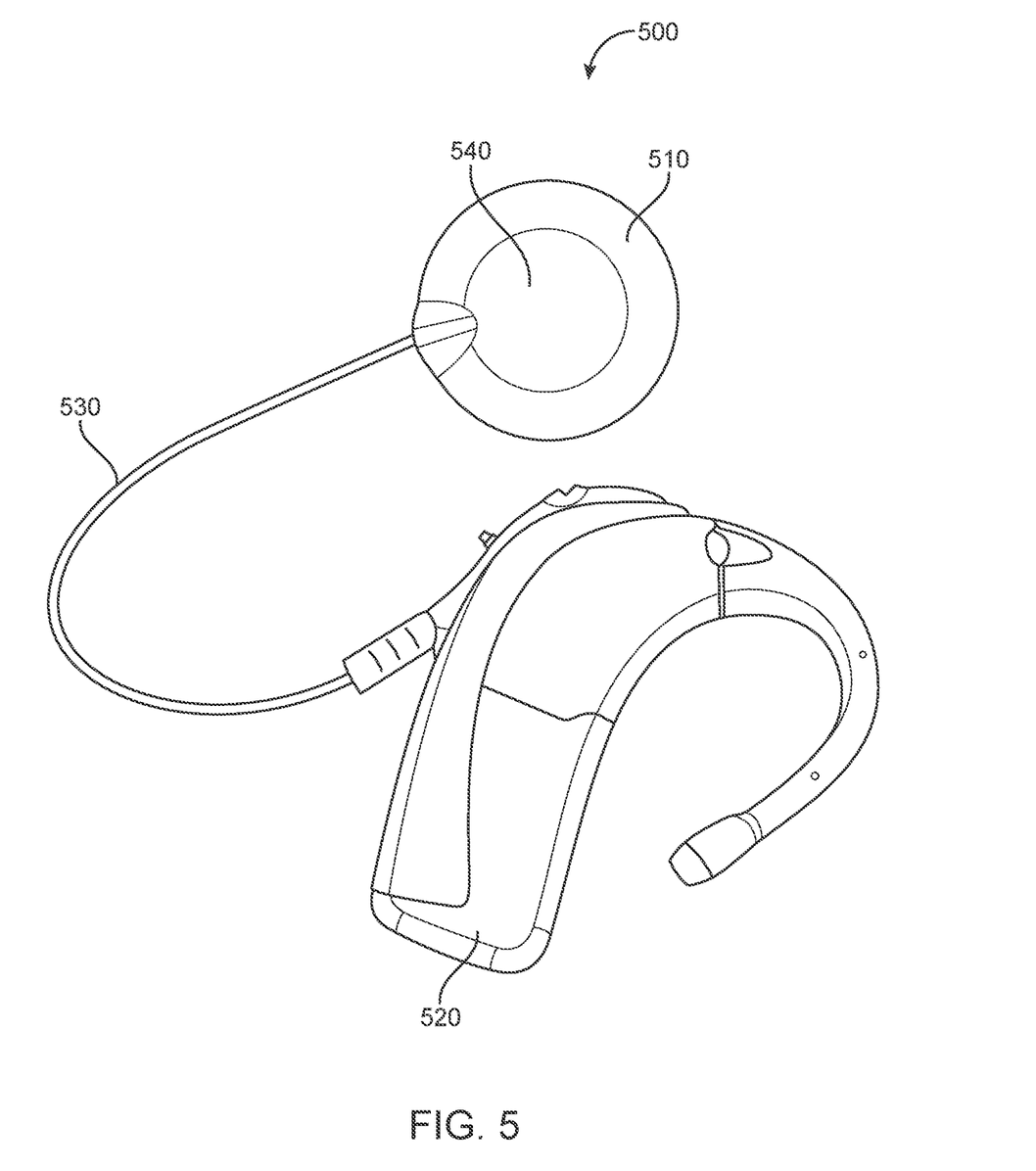

FIG. 5 shows a hearing prosthesis 500 in the form of a cochlear implant 500 with a Behind-The-Ear housing 520 accommodating the hearing prosthesis circuitry similar to the hearing prosthesis circuitry 10 shown in FIG. 1 apart from the fact that the receiver 40 in FIG. 1 has been substituted by signal lines in the cable 530 that transmit the hearing loss compensated output signal 38, see FIG. 1, to a transmitter housing 510.

The transmitter housing 510 is intended to be attached to the head (not shown) of a user and accommodates a near-field magnetic induction communication unit (not visible) that modulates the received hearing loss compensated output signal into a modulated signal suitable for transmission via an embedded ferrite antenna (not visible) that emits a local, non-propagating magnetic field in the direction of a receiver housing (not shown) with field lines aligned for optimum transmission and reception, respectively, with a ferrite core of a ferrite antenna in the receiver housing (not shown) that is implanted underneath the skin opposite the transmitter housing 510 when the transmitter housing 510 is attached to the head of the user. The receiver housing (not shown) provides the received and converted hearing loss compensated audio signal to an electrode (not shown) that is implanted in the cochlea (not shown) of the user.

The magnetic field antenna comprises a coil and a ferrite core for provision of a strong magnetic field at low loss and low cost. The ferrite core is embedded in a multi-layer printed circuit board whereby miniaturization is obtained at low cost.

The coil includes conductive traces formed, e.g. by etching, in a conductive layer of the multi-layer printed circuit board for further ease of manufacture and reduction of cost.

The dotted circle 540 indicates the orientation of the coil having windings around the ferrite core (not visible) of the embedded ferrite antenna (not visible). The orientation of the coil is substantially perpendicular to the longitudinal extension or direction of the ferrite core aligned with the ferrite core of the ferrite antenna in the receiver housing (not shown) implanted inside the head of the human for optimum, or substantially optimum, reception of the transmitted signal.

Parts of conductive layers of the multi-layer printed circuit board may be used to provide magnetic shielding of electronic components such that the components are prevented from disturbing the magnetic field antenna. Shielding can be around other component or around the magnetic field antenna.

The near-field magnetic induction communication unit may also be embedded in the multi-layer printed circuit board facilitating further miniaturisation and cost reduction and ease of electrical interconnection of the near-field magnetic induction communication unit with the magnetic field antenna by conductive traces formed in conductive layers of the multi-layer printed circuit board.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. A hearing prosthesis comprising:
   a hearing loss processor configured to process an audio signal and compensate a hearing loss of a user of the hearing prosthesis, and output a hearing loss compensated audio signal based on the audio signal;
   an output device configured to provide an output signal based on the hearing loss compensated audio signal;
   a near-field magnetic induction communication unit configured for wireless communication; and
   a magnetic field antenna operatively connected with the near-field magnetic induction communication unit;
   wherein the magnetic field antenna comprises a coil and a core surrounded by the coil;
   wherein the core is embedded in a multi-layer printed circuit board; and
   wherein the hearing prosthesis further comprises a dielectric material between a vertical segment of the coil and the core that is surrounded by the coil.

2. The hearing prosthesis according to claim 1, wherein the near-field magnetic induction communication unit is embedded in the multi-layer printed circuit board, and wherein the multi-layer printed circuit board holds conductive traces for electrical interconnection of the near-field magnetic induction communication unit with the magnetic field antenna.

3. The hearing prosthesis according to claim 1, wherein the multi-layer printed circuit board comprises a conductive layer configured for magnetic shielding of the magnetic field antenna.

4. The hearing prosthesis according to claim 1, wherein the hearing loss processor is embedded in the multi-layer printed circuit board.

5. The hearing prosthesis according to claim 1, wherein the coil includes conductive traces formed in a conductive layer of the multi-layer printed circuit board.

6. The hearing prosthesis according to claim 1, wherein the near-field magnetic induction communication unit is configured for provision of the audio signal.

7. The hearing prosthesis according to claim 1, further comprising a microphone configured for conversion of an acoustic signal received at the microphone into the audio signal and, for provision of the audio signal.

8. The hearing prosthesis according to claim 1, further comprising a housing, wherein the magnetic field antenna is positioned in the housing of the hearing prosthesis such that, when the housing is worn at an ear of the user of the hearing prosthesis in its intended position during operation of the hearing prosthesis, a magnetic field generated by the magnetic field antenna will be directed towards an other ear of the user of the hearing prosthesis.

9. The hearing prosthesis according to claim 1, further comprising:
   a transmitter housing to be attached to a head of the user; and
   a receiver housing to be implanted underneath a skin of the user;
   wherein the magnetic field antenna is positioned in the transmitter housing or the receiver housing.

10. The hearing prosthesis according to claim 1, wherein the core comprises a ferrite core.

11. The hearing prosthesis according to claim 1, wherein the output device comprises a receiver.

12. The hearing prosthesis according to claim 1, wherein the output device comprises an electrode of an implant.

13. The hearing prosthesis according to claim 1, wherein the core has a top surface, a first side surface, and a second side surface opposite from the first side surface, and wherein the first side surface and the second side surface of the core are separated from the coil; and
   wherein the dielectric material is between the first side surface of the core and the coil.

14. The hearing prosthesis according to claim 13, further comprising additional dielectric material separating the second side surface of the core from the coil.

15. The hearing prosthesis according to claim 13, wherein the top surface of the core is also separated from the coil.

16. The hearing device according to claim 1, wherein the coil comprises a loop surrounding the core, and wherein the hearing device further includes additional dielectric material disposed between the loop of the coil and the core.

17. A hearing device comprising:
   a hearing loss processor configured to process an audio signal and compensate a hearing loss of a user of the hearing device, and output a hearing loss compensated audio signal based on the audio signal;
   an output device configured to provide an output signal based on the hearing loss compensated audio signal;
   a communication unit; and
   an antenna operatively connected with the communication unit;
   wherein the antenna comprises a coil and a core surrounded by the coil;
   wherein the core is embedded in a multi-layer printed circuit board; and
   wherein the hearing device further comprises a dielectric material between a vertical segment of the coil and the core that is surrounded by the coil.

18. The hearing device according to claim 17, wherein the communication unit comprises a near field magnetic induction communication unit.

19. The hearing device according to claim 17, wherein at least a part of the communication unit is embedded in the multi-layer printed circuit board, and wherein the multi-layer printed circuit board holds conductive traces for electrical interconnection of the communication unit with the antenna.

20. The hearing device according to claim 17, wherein the multi-layer printed circuit board comprises a conductive layer configured for magnetic shielding of the antenna.

21. The hearing device according to claim 17, wherein at least a part of the hearing loss processor is embedded in the multi-layer printed circuit board.

22. The hearing device according to claim 17, wherein the coil includes conductive traces formed in a conductive layer of the multi-layer printed circuit board.

23. The hearing device according to claim 17, further comprising a housing, wherein the antenna is positioned in the housing of the hearing device such that, when the housing is worn at an ear of the user of the hearing device in its intended position during operation of the hearing device, a magnetic field generated by the antenna will be directed towards an other ear of the user of the hearing device.

24. The hearing device according to claim 17, further comprising a receiver accommodated in a receiver housing to be implanted underneath a skin of the user for receiving the hearing loss compensated audio signal, and for providing the hearing loss compensated audio signal to an electrode to be implanted in a cochlea of the user.

25. The hearing device according to claim 17, wherein the output device comprises a receiver.

26. The hearing device according to claim 17, wherein the output device comprises an electrode of an implant.

27. The hearing device according to claim 17, further comprising:
a transmitter housing to be attached to a head of the user; and
a receiver housing to be implanted underneath a skin of the user;
wherein the antenna is positioned in the transmitter housing or the receiver housing.

28. The hearing device according to claim 17, wherein the core has a top surface, a first side surface, and a second side surface opposite from the first side surface, and wherein the first side surface and the second side surface of the core are separated from the coil; and
wherein the dielectric material is between the first side surface of the core and the coil.

29. The hearing device according to claim 28, further comprising additional dielectric material separating the second side surface of the core from the coil.

30. The hearing device according to claim 28, wherein the top surface of the core is also separated from the coil.

31. The hearing device according to claim 28, wherein the coil comprises a loop surrounding the core, and wherein the hearing device further includes additional dielectric material disposed between the loop of the coil and the core.

32. A hearing device comprising:
a hearing loss processor configured to process an audio signal and compensate a hearing loss of a user of the hearing device, and output a hearing loss compensated audio signal based on the audio signal;
an output device configured to provide an output signal based on the hearing loss compensated audio signal;
a communication unit; and
an antenna operatively connected with the communication unit;
wherein the antenna comprises a coil and a core;
wherein the core is embedded in a multi-layer printed circuit board; and
wherein the coil comprises a loop surrounding the core, and wherein the hearing device further comprises a dielectric material between the loop of the coil and the core that is surrounded by the loop of the coil.

33. The hearing device according to claim 32, wherein the communication unit comprises a near field magnetic induction communication unit.

34. The hearing device according to claim 32, wherein at least a part of the communication unit is embedded in the multi-layer printed circuit board, and wherein the multi-layer printed circuit board holds conductive traces for electrical interconnection of the communication unit with the antenna.

35. The hearing device according to claim 32, wherein the multi-layer printed circuit board comprises a conductive layer configured for magnetic shielding of the antenna.

36. The hearing device according to claim 32, wherein at least a part of the hearing loss processor is embedded in the multi-layer printed circuit board.

37. The hearing device according to claim 32, wherein the coil includes conductive traces formed in a conductive layer of the multi-layer printed circuit board.

38. The hearing device according to claim 32, further comprising a housing, wherein the antenna is positioned in the housing of the hearing device such that, when the housing is worn at an ear of the user of the hearing device in its intended position during operation of the hearing device, a magnetic field generated by the antenna will be directed towards an other ear of the user of the hearing device.

39. The hearing device according to claim 32, further comprising a receiver accommodated in a receiver housing to be implanted underneath a skin of the user for receiving the hearing loss compensated audio signal, and for providing the hearing loss compensated audio signal to an electrode to be implanted in a cochlea of the user.

40. The hearing device according to claim 32, wherein the output device comprises a receiver.

41. The hearing device according to claim 32, wherein the output device comprises an electrode of an implant.

42. The hearing device according to claim 32, further comprising:
a transmitter housing to be attached to a head of the user; and
a receiver housing to be implanted underneath a skin of the user;
wherein the antenna is positioned in the transmitter housing or the receiver housing.

* * * * *